(12) United States Patent
Shia et al.

(10) Patent No.: US 7,097,632 B2
(45) Date of Patent: Aug. 29, 2006

(54) AUTOMATIC VALVE

(75) Inventors: Benedict Shia, Needham, MA (US); James Christopher Bailey, Yellow Springs, OH (US)

(73) Assignee: Sherwood Services AG, (CH)

( * ) Notice: Subject to any disclaimer, the term of this patent is extended or adjusted under 35 U.S.C. 154(b) by 159 days.

(21) Appl. No.: 10/281,638

(22) Filed: Oct. 28, 2002

(65) Prior Publication Data

US 2004/0082909 A1    Apr. 29, 2004

(51) Int. Cl.
*A61J 7/00* (2006.01)

(52) U.S. Cl. ............ 604/77; 604/167.01; 604/244

(58) Field of Classification Search ......... 604/167.01, 604/167.05, 244–256
See application file for complete search history.

(56) References Cited

U.S. PATENT DOCUMENTS

| 2,335,085 | A | | 11/1943 | Roberts ............... 251/107 |
| 3,889,675 | A | | 6/1975 | Stewart ............... 128/240 |
| 3,957,082 | A | | 5/1976 | Fuson et al. .......... 137/625.41 |
| 4,082,095 | A | | 4/1978 | Mendelson et al. ...... 128/235 |
| 4,112,932 | A | * | 9/1978 | Chiulli ............... 604/264 |
| 4,573,965 | A | | 3/1986 | Russo ................ 604/30 |
| 4,729,401 | A | * | 3/1988 | Raines ............... 137/512 |
| 4,735,607 | A | | 4/1988 | Keith, Jr. ............ 604/54 |
| 4,790,832 | A | | 12/1988 | Lopez ................ 604/283 |
| 4,895,562 | A | | 1/1990 | Lopez ................ 604/48 |
| 5,256,160 | A | | 10/1993 | Clement .............. 604/319 |
| 5,261,459 | A | | 11/1993 | Atkinson et al. ....... 137/846 |
| 5,328,478 | A | | 7/1994 | McVay ............... 604/147 |
| 5,395,352 | A | | 3/1995 | Penny ................ 604/256 |
| 5,417,664 | A | | 5/1995 | Felix et al. .......... 604/129 |
| 5,540,668 | A | | 7/1996 | Wilson, Jr. et al. .... 604/248 |
| 5,738,648 | A | | 4/1998 | Lands et al. .......... 604/35 |
| 6,461,335 | B1 | | 10/2002 | Noecker .............. 604/246 |
| 6,551,270 | B1 | * | 4/2003 | Bimbo et al. ......... 604/93.01 |

* cited by examiner

*Primary Examiner*—Kevin C. Sirmons
*Assistant Examiner*—Jaime Corrigan

(57) ABSTRACT

A valve system is provided that includes a valve connector that has a portion of a first passageway. The valve connector includes a suction port and an introduction port that are spaced apart and in substantially parallel alignment. The suction port and the introduction port are manipulable to establish fluid communication between the portion of the first passageway and the suction port or the introduction port. The valve connector may have a rotatable outer cap that includes the suction port and the introduction port. The cap being configured to facilitate manipulation of the suction port and the introduction port for establishing fluid communication with the portion of the first passageway. The introduction port may include a normally closed valve. The valve connector may be attached to a dual lumen nasogastric tube. In an alternate embodiment, the valve connector further includes a portion of a second passageway that includes a relief port. The relief port can include a one-way valve.

8 Claims, 4 Drawing Sheets

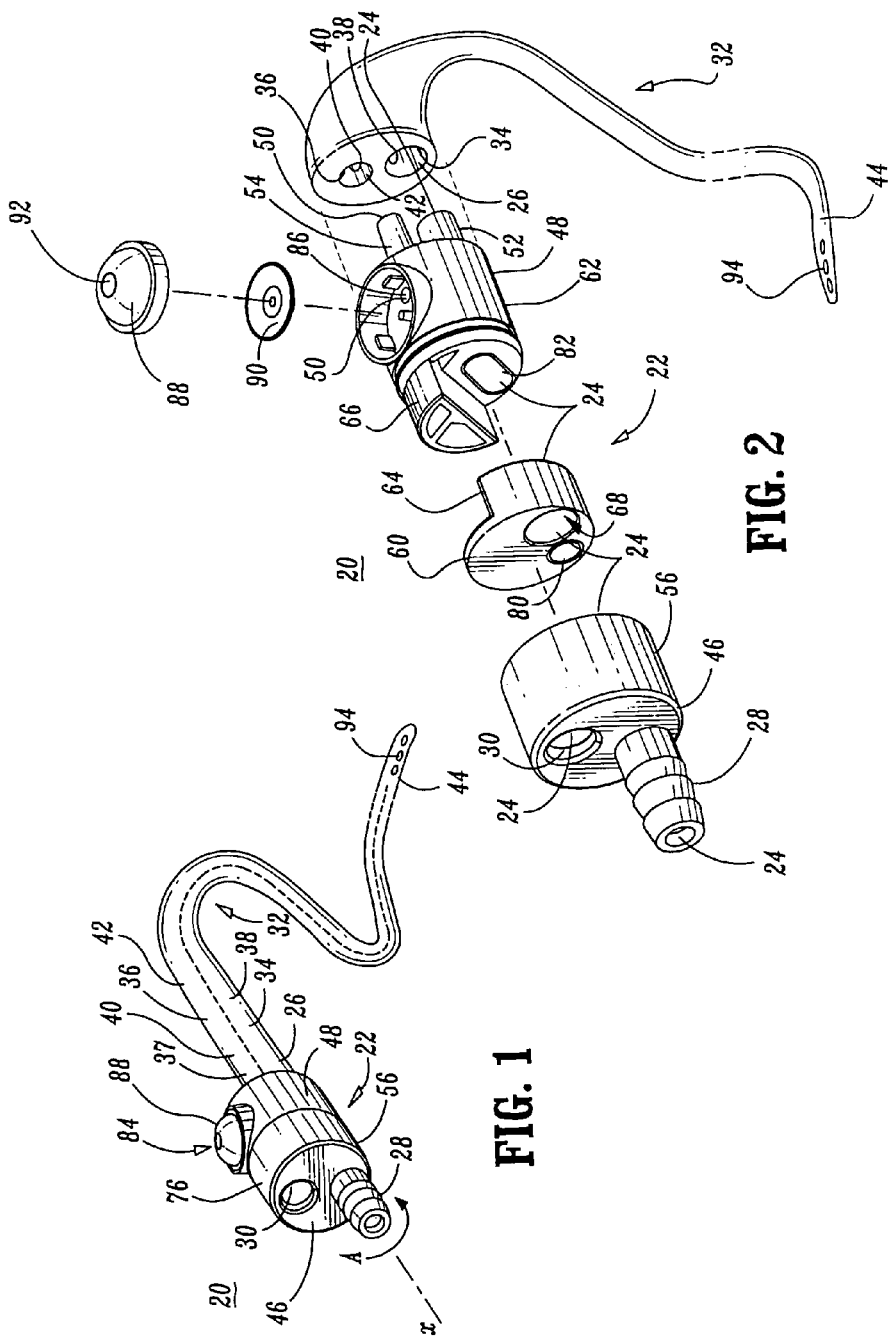

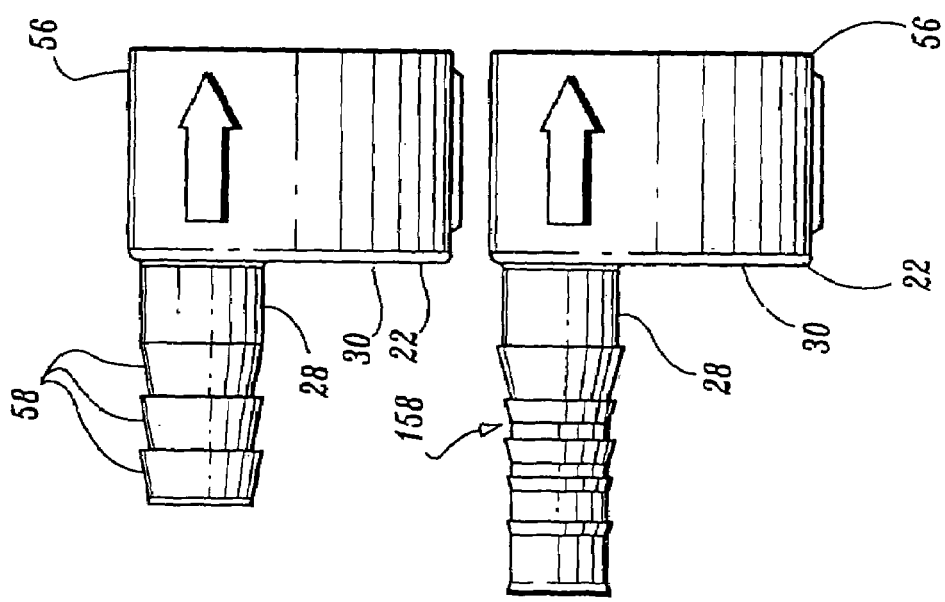
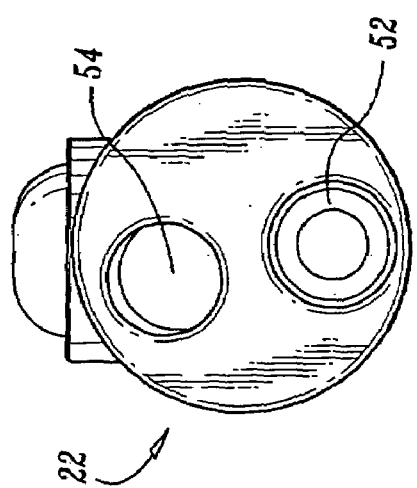

AUTOMATIC VALVE

BACKGROUND

1. Technical Field

The present disclosure generally relates to medical administration of fluids with a subject, and more particularly, to a valve system, having multiple ports, which is manipulated to establish fluid communication with a passageway of a nasogastric tube.

2. Description of the Related Art

Medical systems inserted with a body of a subject for the administration of fluids with the subject, such as, for example, nasogastric tubing are known in the art. Nasogastric tubing is typically employed in hospitals, nursing homes, care facilities, etc. to remove fluids from the body of the subject, such as, for aspirating fluids from a gastrointestinal tract (GI tract) of the subject or to introduce nutrients, supplements, medicines, etc. to the subject.

In one application, nasogastric tubing aspirates fluid and air to decompress the contents of the subject's stomach to avoid damaging the inner wall, e.g., the gastric mucosa. Nasogastric tubing may also facilitate removal of accumulated fluids, blood, etc. from the GI tract due to disease, intestinal obstruction, bleeding ulcers and paralytic ulcers to prevent progressive distension of the GI tract. Progressive distension of the GI tract can lead to shock, visceral injury and vomiting. Vomit may be aspirated into the respiratory tract and cause asphyxia and pneumoma.

Nasogastric tubes are employed with subjects undergoing abdominal surgery to keep the stomach vacant of fluid and postoperatively to prevent complications, such as, decreased gastrointestinal function. Such nasogastric tubing advantageously prevents pooling of liquids in the GI tract to facilitate postoperative recovery of digestive function. Nasogastric tubing can also be employed to protect gastric suture lines, preventing and treating paralytic ileus, treating drug overdoses, lavage, as well as other conditions that affect the GI tract.

In conventional use, a flexible plastic nasogastric tube is employed. The nasogastric tube defines a passageway that extends from a proximal end to a distal end. A practitioner introduces the distal end of the nasogastric tube through a nasal canal of a subject via one of the nostrils. The distal end is passed through the pharynx and down the esophagus into the GI tract. The distal end can be passed into the duodenum, stomach, etc. depending on the particular application such as, for example, aspirating fluids, introduction for medication, feeding, etc. Several openings are formed in the distal end that permit passage of gastric fluids, nutrients, medication, etc.

To prevent blockage of the openings in the distal end, a dual lumen nasogastric tube is generally used. The dual lumen nasogastric tube includes a suction/irrigation lumen and a separate vent lumen. The suction/irrigation lumen is connected to a suction source providing either intermittent or continuous suction to facilitate suction drainage and irrigation. The vent lumen communicates with the suction/irrigation lumen adjacent the distal end of the nasogastric tubing to permit atmospheric air to be drawn through the vent lumen into the suction lumen. The flow of atmospheric air moderates the amount of suction and flow during aspiration. Nutrients or medication introduced is passed down the suction lumen and the vent lumen is clamped or plugged. Air pressure is applied thereafter to clear the vent lumen.

The proximal end of the nasogastric tube exits the nostril and communicates with a suction source. The proximal end may be connected to the suction source, a feeding pump, etc. through a connector that may communicate with a collection vessel. In a fluid aspirating application, stomach fluids are drawn through the openings in the distal end, through the passageway and into the collection vessel, as facilitated by the suction source. In a fluid introduction application, nutrients, medication, etc. are injected into the passageway and forced through the openings in the distal end and into for example, the duodenum.

The connector is connected to a second tube that is connected to the suction source, or alternatively, to a feeding pump. Frequently, the nasogastric tubing must be alternated to a source for suction, feeding or introduction of an injection. To alternate the nasogastric tubing application, the second tube is removed from the connector or the connector is removed from the proximal end of the nasogastric tubing and the desired connection is made. These known devices and methods suffer from many drawbacks. Typically, the practitioner is spattered with vomit or other fluid during disconnection of the tubing and connector.

This procedure may also require clamping of the tubing. This is disadvantageously cumbersome, unclean and does not adequately prevent leakage of GI tract fluids. Leaking and splattering intestinal fluids can cause contamination of wounds, tubing and catheters. The intestinal fluids may contain infectious material that poses serious health risks to the practitioner.

Another drawback of these devices and methods is the labor intensive burden of cleaning the leaking and splattering intestinal fluids. Patient discomfort and complication may also result. This consumes a great deal of practitioner time and adds to the cost of healthcare.

Therefore, it would be desirable to overcome the disadvantages and drawbacks of the prior art with a valve system, having multiple ports, which is manipulated to establish fluid communication with a passageway of a nasogastric tube to avoid leakage of intestinal fluids and minimize disease propagation. It would be desirable if such a valve system included a rotatable cap that is manipulated to facilitate connection of the passageway of the nasogastric tube with alternate sources to achieve the principles of the present disclosure. It would be highly desirable if the valve system is connected to a second passageway of the nasogastric tube. It is contemplated that the valve system and its constituent parts are easily and efficiently manufactured and assembled.

SUMMARY

Accordingly, a valve system, having multiple ports, is provided that is manipulated to establish fluid communication with a passageway of a nasogastric tube to avoid leakage of intestinal fluids and minimize disease propagation to overcome the disadvantages and drawbacks of the prior art. Desirably, such a valve system includes a rotatable cap that is manipulated to facilitate connection of the passageway of the nasogastric tube with alternate sources to achieve the principles of the present disclosure. Most desirably, the valve system is connected to a second passageway of the nasogastric tube. The valve system is easily and efficiently manufactured and assembled. The present disclosure resolves related disadvantages and drawbacks experienced in the art.

In one particular embodiment, in accordance with the principles of the present disclosure, a valve system is provided including a valve connector that has a portion of a first passageway. The valve connector includes a suction port and an introduction port that are spaced apart and in substantially parallel alignment. The suction port and the introduction port are manipulable to establish fluid communication between the portion of the first passageway and the suction port or the introduction port. The valve connector may have a rotatable outer cap that includes the suction port and the introduction port. The cap is configured to facilitate manipulation of the suction port and the introduction port for establishing fluid communication with the portion of the first passageway.

The introduction port may include a normally closed valve. The normally closed valve can include an elastically deformable septum having an elongate slit formed through a thickness of the septum. The septum may be elastically deformable such that a cannula is engageable with the elongate slit to establish fluid communication between the cannula and the first passageway. The septum may be recessed relative to an outer surface of the valve connector. The valve connector may define a recessed cylindrical cavity, the cylindrical cavity including the septum. The septum may have an angular orientation relative to a longitudinal axis of the cylindrical cavity.

Alternatively, the valve connector defines a longitudinal axis and the portion of the first passageway defines an angled flow path. In another embodiment, the suction port and the insertion port are manipulable to establish fluid communication between the portion of the first passageway and the suction port and the insertion port.

The valve connector may be attached to a dual lumen nasogastric tube. In an alternate embodiment, the valve connector further includes a portion of a second passageway that includes a relief port. The relief port can include a one-way valve. The portion of the first passageway and a portion of the second passageway disposed within the valve connector fluidly communicate with the nasogastric tube. In another embodiment, the first passageway and the second passageway do not fluidly communicate within the valve connector.

In an alternate embodiment, a nasogastric valve system has a nasogastric tube including a first lumen and a second lumen. The first lumen defines a first portion of a first passageway. The second lumen defines a first portion of a second passageway. The first passageway and the second passageway fluidly communicate adjacent a distal end of the nasogastric tube. A valve connector having a first end and a second end are attached to the nasogastric tube. The valve connector includes a second portion of the first passageway and a second portion of the second passageway. The valve connector further includes a suction port and an introduction port that are spaced apart and in substantially parallel alignment. The suction port and the introduction port are manipulable to establish fluid communication between the second portion of the first passageway and the suction port or the introduction port. The introduction port defines a normally closed valve and the second portion of the second passageway defines a relief port.

In another alternate embodiment, the valve system has the portion of the first passageway and the portion of the second passageway being in fluid communication.

In yet another embodiment, a method for administration of fluids with a subject is provided. The method includes the steps of: providing a valve system, similar to those described; attaching a nasogastric tube, similar to those described, to the valve connector; inserting a distal end of the nasogastric tube into the subject via a passage of the subject; and manipulating a suction port and a introduction port of a valve connector of the valve system to establish fluid communication between a second portion of a first passageway of the nasogastric tube and the suction port or the introduction port.

The step of providing a valve system may further include a valve connector having a rotatable cap. The cap includes the suction port and the introduction port such that the step of manipulating includes rotating the cap to establish fluid communication with the suction port for removing fluid from the subject. Alternatively, the step of manipulating includes rotating the cap to establish fluid communication with the introduction port for injecting fluid with the subject.

BRIEF DESCRIPTION OF THE DRAWINGS

The objects and features of the present disclosure, which are believed to be novel, are set forth with the particularity in the appended claims. The present disclosure, both as to its organization and manner of operation, together with further objectives and advantages, may be best understood by reference to the following description, taken in connection with the accompanying drawings, which are described below.

FIG. 1 is a perspective view of one embodiment of a valve system, in accordance with the principles of the present disclosure;

FIG. 2 is a perspective view of the valve system shown in FIG. 1, with parts separated;

FIG. 3 is a front view of a distal end of a valve of the valve system shown in FIG. 1;

FIG. 4 is a cutaway side view of a proximal end of the valve shown in FIG. 1;

FIG. 5 is a cutaway side view of an alternate embodiment of the proximal end shown in FIG. 4;

DETAILED DESCRIPTION OF EXEMPLARY EMBODIMENTS

Figure 10:
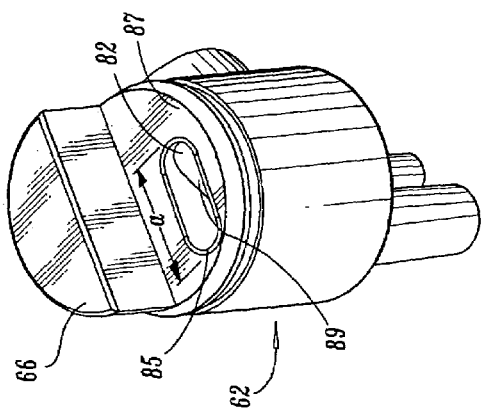
FIG. 10 is a perspective view of a body of the valve shown in FIG. 1.

The exemplary embodiments of the valve system and methods of use disclosed are discussed in terms of medical systems inserted with a body of a subject for the administration of fluids, and more particularly, in terms of a valve system, having multiple ports, which is manipulated to establish fluid communication with a passageway of a nasogastric tube to avoid leakage of intestinal fluids and minimize disease propagation. It is envisioned that the present disclosure finds application for the removal of fluids from a body of the subject, such as aspirating fluids from the body or to introduce nutrients, supplements, medicines, etc. to the body. It is further envisioned that the valve system may be used with nasogastric tubing to decompress the contents of the subject's stomach and facilitate removal of accumulated fluids, blood, etc. from the GI tract due to disease, intestinal obstruction, bleeding ulcers and paralytic ulcers. It is contemplated that the valve system may be used with nasogastric tubing for abdominal surgery to keep the stomach vacant of fluid and postoperatively to prevent complications, such as, decreased gastrointestinal function. It is further contemplated that the valve system finds application in protecting gastric suture lines, preventing and treating paralytic ileus, treating drug overdoses, lavage, as well as other conditions that affect the GI tract. A practitioner may employ such a valve system in hospitals, nursing homes, care facilities, etc.

In the discussion that follows, the term "proximal" will refer to the portion of a structure that is closer to a practitioner, while the term "distal" will refer to the portion that is further from the practitioner. As used herein, the term "subject" refers to a human patient or other animal having fluids administered therewith, including removal and introduction as discussed herein. According to the present disclosure, the term "practitioner" refers to a doctor, nurse, or other care provider utilizing the valve system with medical tubing, and may include support personnel.

Reference will now be made in detail to the exemplary embodiments of the present disclosure, which are illustrated in the accompanying figures. Turning now to the figures wherein like components are designated by like reference numerals throughout the several views and initially to FIGS. 1 and 2, there is illustrated a nasogastric valve system 20, in accordance with the principles of the present disclosure.

Nasogastric valve system 20 includes a valve connector 22 that defines a longitudinal axis x and includes a second portion 24 of a first passageway 26. Valve connector 22 further includes a suction port 28 and an introduction port 30 that are spaced apart and in substantially parallel alignment. Suction port 28 and introduction port 30 are manipulable to establish fluid communication between portion 24 of first passageway 26 and suction port 28 or introduction port 30. This configuration advantageously avoids leakage of intestinal fluids and minimizes disease propagation, as will be discussed herein.

The component portions of valve connector 22, which may be disposable, are fabricated from materials suitable for nasogastric tubing applications for the administration of fluids with a subject including removal and introduction. These materials may include suitable medical grade, flexible, semi-rigid and rigid plastic materials, which may incorporate polyvinylchloride (PVC), silicone, etc., as well as medical grade metals, such as stainless steel and aluminum, depending on the particular nasogastric tubing application and/or preference of a practitioner. One skilled in the art, however, will realize that other materials and fabrication methods suitable for assembly and manufacture, in accordance with the present disclosure, also would be appropriate.

Nasogastric valve system 20 includes a flexible nasogastric tube 32 that has a fluid lumen 34 and a vent lumen 36. Fluid lumen 34 and vent lumen 36 are disposed in a side-by-side, parallel relationship and extend from a proximal end 37 to a distal end 44 of nasogastric tube 32. It is contemplated that nasogastric tube 32 may be monolithically formed or, alternatively, fluid lumen 34 and vent lumen 36 may be separately formed and integrally joined thereafter. It is further contemplated that fluid lumen 34 and vent lumen 36 may not be attached.

Fluid lumen 34 is configured to aspirate fluids from a GI tract of the subject (not shown) or to introduce nutrients, supplements, medicines, etc. to the subject. Vent lumen 36 is configured to regulate the amount of suction and flow during aspiration.

The component portions of nasogastric tube 32, which may be disposable, are fabricated from materials suitable for nasogastric tubing applications for the administration of fluids with a subject including removal and introduction. These materials may include suitable medical grade, flexible and semi-rigid plastic materials, which may incorporate polyvinylchloride (PVC), silicone, etc., as well as medical grade flexible metal structure, depending on the particular nasogastric tubing application and/or preference of a practitioner. One skilled in the art, however, will realize that other materials and fabrication methods suitable for assembly and manufacture, in accordance with the present disclosure, also would be appropriate.

Fluid lumen 34 defines a first portion 38 of first passageway 26. Vent lumen 36 defines a first portion 40 of a second passageway 42. First passageway 26 and second passageway 42 fluidly communicate adjacent a distal end 44 of nasogastric tube 32. It is envisioned that first passageway 26 and second passageway 42 do not fluidly communicate apart from distal end 44. Alternatively, first passageway 26 and second passageway 42 may fluidly communicate within valve connector 22 via appropriate structure, such as, for example, a connecting cavity, opening, etc. that facilitates communication therebetween.

Valve connector 22 has a first end, such as, for example, proximal end 46 and a second end, such as, for example distal end 48. Referring to FIG. 3, distal end 48 includes a fluid port 52 and a vent port 54. Distal end 48 is attached to proximal end 37 of nasogastric tube 32 such that fluid port 52 and vent port 54 are received by fluid lumen 34 and vent lumen 36, respectively. Fluid port 52 and vent port 54 slidably engage respective interior surfaces of fluid lumen 34 and vent lumen 36 in a frictional interference fit to maintain a fluid sealing engagement between valve connector 22 and nasogastric tube 32. Valve connector 22 includes second portion 24 of first passageway 26 and a second portion 50 of second passageway 42.

Referring to FIGS. 4–7, valve connector 22 has a rotatable cylindrical outer cap 56 that includes suction port 28 and introduction port 30. Cap 56 is configured to facilitate manipulation of suction port 28 and introduction port 30 for establishing fluid communication with second portion 24 of first passageway 26. Cap 56 may have various cross-sectional configurations such as, for example, rectangular, polygonal, etc. to facilitate manipulation thereof. It is envisioned that cap 56 may be variably dimensioned with regard to, for example, diameter, length, etc. according to the requirements of a particular application.

Cap 56 is manually rotated by the practitioner, in the direction shown by arrow A (counter clockwise) in FIG. 1, to establish fluid communication between suction port 28 and first passageway 26 for aspirating fluids through fluid lumen 34. Alternatively, cap 56 is manually rotated by the practitioner, in the direction shown by arrow B (clockwise) in FIG. 11, to establish fluid communication between introduction port 30 and first passageway 26 for introducing nutrients, supplements, medicines, etc. to the subject. Cap 56 is rotatable through an angle of approximately 120 degrees to alternate fluid communication from suction port 28 to introduction port 30.

It is contemplated that cap 56 may be rotated clockwise and counter clockwise, in varying degrees of rotation through an angle up to and including 360 degrees, to establish fluid communication between suction port 28 or introduction port 30 and first passageway 26. It is further contemplated that cap 56 may be manipulated axially, angularly rotated relative to longitudinal axis x, etc. to establish fluid communication. It is envisioned that cap 56 may be rotated by mechanical, motorized, computerized, etc. devices to establish fluid communication with suction port 28 and introduction port 30, in accordance with the principles of the present disclosure.

Suction port 28 extends axially along longitudinal axis x and is configured for reception by suction tubing (not shown), which is connected to a source of suction (not shown), such as, for example, a vacuum pump, etc. Suction port 28 has a series of flanges 58, as shown in FIG. 4. Flanges 58 form a barb-like configuration to retain the suction tubing therewith. It is contemplated that the series of flanges 58 may be arranged in diameters that are uniform, increasing, decreasing, etc. to facilitate retention, according to the particular application. As shown in FIG. 5, an alternate embodiment of suction port 28 is shown, which includes flanges 158 that are arranged in an order of decreasing diameter.

Figure 9:
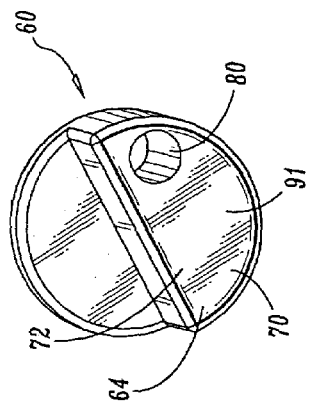
FIG. 9 is a bottom perspective view of the part shown in FIG. 8.
Figure 7:
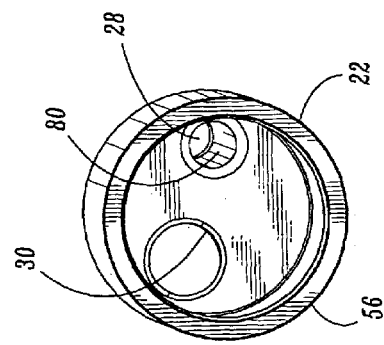
FIG. 7 is a bottom perspective of the cap shown in FIG. 6.
Figure 8:
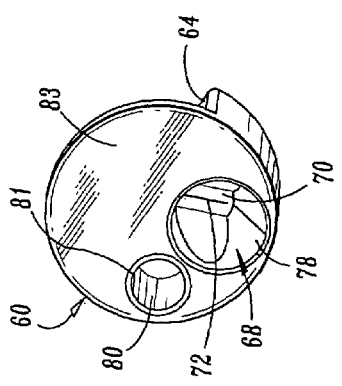
FIG. 8 is a top perspective view of a part of the valve shown in FIG. 1.
Figure 6:
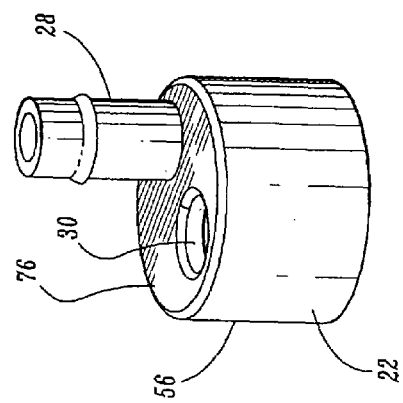
FIG. 6 is a side perspective view of a cap of the valve shown in FIG. 1.

Referring to FIGS. 8–10, valve connector 22 includes a part 60 and a body 62. Part 60 is disposed within cap 56 and has a stepped portion 64 that is configured to engage and fit with a correspondingly configured stepped portion 66 of body 62. Part 60 is fabricated from an elastomeric material such as, for example, rubber, etc. and configured to facilitate manipulation of cap 56 to establish fluid communication between suction port 28 or introduction port 30 and first passageway 26. Cap 56 rotates relative to part 60 to align suction port 28 or introduction port 30 with first passageway 26 as desired, and will be discussed further below. The elastomeric material of part 60 enables sealing of first passageway 26 during fluid communication. It is envisioned that part 60 may be fabricated from less flexible plastics or suitable metals.

Introduction port 30 includes a normally closed valve 68 that is formed in part 60. Normally closed valve 68 includes an elastically deformable septum 70 having an elongate slit 72 formed through a thickness of septum 70. It is contemplated that all or only portions of septum 70 may be elastically deformable.

Figure 12:
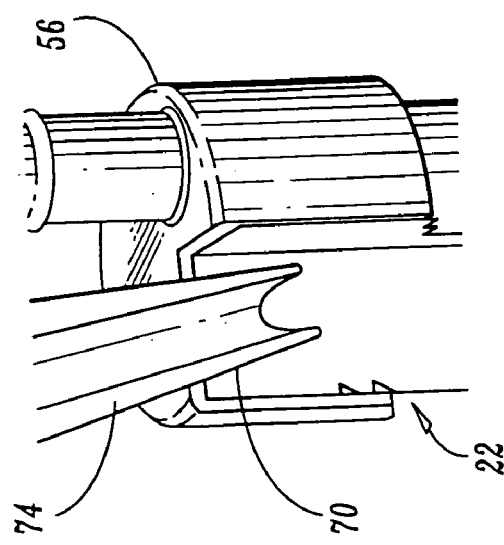
FIG. 12 is a cutaway perspective view of the valve system shown in FIG. 11 having a cannula inserted therewith.

Septum 70 is elastically deformable such that a cannula 74 (FIG. 12) is engageable with elongate slit 72 to establish fluid communication between cannula 74 and first passageway 26 for introducing nutrients, supplements, medicines, etc. to the subject. Septum 70 has an angular orientation relative to longitudinal axis x to facilitate passing cannula 74 through slit 72. It is envisioned that septum 70 may be oriented at various angular orientations relative to longitudinal axis x, such as, for example, acute, perpendicular, etc. A feeding pump or the like may be introduced with introduction port 30 via septum 70 for constant or intermittent feeding of the subject.

Septum 70 is recessed relative to an outer surface 76 of valve connector 22. Valve connector 22 and normally closed valve 68 cooperate to define a recessed cylindrical cavity 78. It is contemplated that valve connector 22 or normally closed valve 68 may individually define cavity 78. Cavity 78 includes septum 70.

Part 60 includes a suction opening 80. Suction opening 80 facilitates communication between suction port 28 and first passageway 26. A raised lip 81 is circumferentially disposed, on a surface 83 of part 60, about suction opening 80. Surface 83 is configured for abutting engagement with the interior surface of cap 56 such that raised lip 81 facilitates sealing and prevents leakage of nasogastric valve system 20.

For example, cap 56 is manually rotated, in the direction shown by arrow A (counter clockwise) in FIG. 1, to establish fluid communication between suction port 28 and first passageway 26. Raised lip 81 is snug fit with the opening of suction port 28 in cap 56 to facilitate seating of cap 56 with part 60. This configuration prevents leakage from first passageway 26 during suction. It is contemplated that tactile feedback is provided to a practitioner via a snap, etc. fitting engagement of raised lip 81 with suction port 28, to indicate fluid communication is established between suction port 28 and first passageway 26. It is further contemplated that such tactile feedback indicates seating of suction port 28 with suction opening 80 and sealing of first passageway 26.

Figure 11:
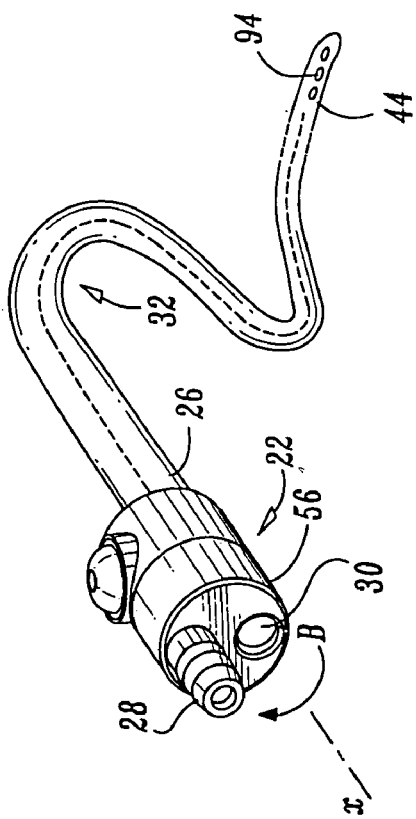
FIG. 11 is a perspective view of the valve system having the cap rotated for introduction.

Alternatively, cap 56 is manually rotated, in the direction shown by arrow B (clockwise) in FIG. 11, to establish fluid communication between introduction port 30 and first passageway 26. In this orientation, raised lip 81 engages the interior surface of cap 56 to seal off suction opening 80. This configuration prevents vacuum leakage from suction port 28 during fluid communication between introduction port 30 and first passageway 26. It is envisioned that raised lip 81 may have various geometries, thickness, height, etc. according to the requirements of a particular application. It is further envisioned that raised lip 81 may be variously disposed about suction opening 80 such as, for example, intermittent, undulating, etc.

Normally closed valve 68 is disposed adjacent to suction opening 80 for alignment with an angled flow path 82 of body 62. Flow path 82 has a width a of sufficient dimension such that suction opening 80 and normally closed valve 68 of part 60 are concurrently positioned into alignment therewith. This configuration advantageously facilitates establishing fluid communication with suction port 28 or introduction port 30 upon rotation of cap 56 relative to part 60. As suction opening 80 and normally closed valve 68 are in alignment with first passageway 26, suction port 28 or introduction port 30 can be manipulated, as desired for removing or introducing fluids to the subject. It is contemplated that suction port 28 and insertion port 30 are manipulable to establish fluid communication between first passageway 26 and suction port 28 and insertion port 30 concurrently.

A raised lip 85 is disposed, on a surface 87 of body 62, about an opening 89 of angled flow path 82. Surface 87 is configured for abutting engagement with a surface 91 of part 60 such that raised lip 85 facilitates sealing and prevents leakage of nasogastric valve system 20. Raised lip 85 engages surface 91 to prevent leakage from first passageway 26 during use. It is envisioned that raised lip 85 may have various geometries, thickness, height, etc. according to the requirements of a particular application. It is further envisioned that raised lip 85 may be variously disposed about angled flow path 82 such as, for example, intermittent, undulating, etc.

Referring back to FIGS. 1 and 2, second portion 50 of second passageway 42 includes a relief port 84. Relief port 84 is disposed with valve connector 22 and protrudes from outer surface 76. Relief port 84 includes an opening 86 that communicates with second passageway 42 and vent lumen 36. Vent lumen 36, second passageway 42 and relief port 84 are configured to regulate the amount of suction and flow during aspiration. It is contemplated that relief port 84 may be employed to clear nasogastric tube 32. A cap 88 and valve 90 are mounted with relief port 84. Cap 88 defines an opening 92 that is configured to receive a cannula (not shown) or the like, which communicates with vent lumen 36. It is contemplated that relief port 84 may be connected to atmospheric air, venting source, etc. It is further contemplated that cap 88 may include a one-way valve, bi-directional valve, etc.

In operation, a valve system 20, similar to that described in accordance with the principles of the present disclosure is provided for administration of fluids with a subject. The components of valve system 20 including valve connector 22 and nasogastric tube 32, similar to those described, are fabricated, properly sterilized and otherwise prepared for storage, shipment and use. Nasogastric tube 32 is manipulated such that fluid lumen 34 and vent lumen 36 receive fluid port 52 and vent port 54, respectively, as discussed. Thus, nasogastric tube 32 is attached to valve connector 22 so that second portion 24 and first portion 38 of first passageway 26 fluidly communicate. Second portion 50 and first portion 40 of second passageway 42 also fluidly communicate.

A practitioner introduces distal end 44 of nasogastric tube 32 through a nasal canal of a subject (not shown) via one of the nostrils. Distal end 44 is passed through the pharynx and down the esophagus into the GI tract. Distal end 44 can be passed into the duodenum, stomach, etc. depending on the particular application such as, for example, aspirating fluids, introduction for medication, feeding, etc. Several openings 94 are formed in distal end 44 that permit passage of gastric fluids, nutrients, medication, etc.

Cap 56 is rotated such that suction port 28 and introduction port 30 are manipulated to establish fluid communication between second portion 24 of first passageway 26 and suction port 28 or introduction port 30, as desired. Referring to FIG. 1, cap 56 is manually rotated by the practitioner, in the direction shown by arrow A (counter clockwise), to establish fluid communication between suction port 28 and first passageway 26 for aspirating fluids through fluid lumen 34 from the body of the subject. Raised lip 81 snugly fits with the opening of suction port 28 in cap 56, as described, providing tactile feedback to the practitioner that fluid communication is established and first passageway 26 is sealed. Valve system 20 may be connected to a collection vessel or the like to retain collected fluids.

Referring to FIG. 11, alternatively, cap 56 is manually rotated by the practitioner, in the direction shown by arrow B (clockwise), to establish fluid communication between introduction port 30 and first passageway 26 for injecting fluids. Raised lip 81 engages the interior surface of cap 56 to seal off suction opening 80, as described. In one embodiment, cannula 74 is inserted with normally closed valve 68, as discussed, to introduce nutrients, supplements, medicines, etc. to the body of the subject. Valve system 20 may be connected to a feeding pump or the like to provide constant or intermittent feeding. This configuration advantageously avoids leakage of intestinal fluids and minimizes disease propagation.

It is contemplated that nasogastric valve system 20 includes the necessary electronics and/or processing components to perform fluid measurement and analysis to facilitate diagnosis, treatment, etc. of a subject, as is known to one skilled in the art.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A nasogastric valve system comprising:
    a nasogastric tube including a first lumen and a second lumen, the first lumen defining a first portion of a first passageway, the second lumen defining a first portion of a second passageway, wherein the first passageway and the second passageway fluidly communicate adjacent a distal end of the nasogastric tube; and
    a valve connector having a first end and a second end attached to the nasogastric tube, the valve connector including a second portion of the first passageway and a second portion of the second passageway, the valve connector further including a suction port and an introduction port that are spaced apart and in substantially parallel alignment, the suction port and the introduction port being manipulable to establish fluid communication between the second portion of the first passageway and the suction port or the introduction port, the introduction port defining a normally closed valve and the second portion of the second passageway defining a relief port.

2. A valve system as recited in claim 1, wherein the valve connector has a rotatable outer cap that includes the suction port and the introduction port, the cap being configured to facilitate manipulation of the suction port and the introduction port for establishing fluid communication with the second portion of the first passageway.

3. A valve system as recited in claim 1, wherein the normally closed valve includes an elastically deformable septum having an elongate slit formed through a thickness of the septum.

4. A valve system as recited in claim 3, wherein the septum is elastically deformnable such that a cannula is engageable with the elongate slit to establish fluid communication between the cannula and the first passageway.

5. A valve system as recited in claim 1, wherein the valve connector defines a longitudinal axis and the second portion of the first passageway defines an angled flow path.

6. A method for administration of fluids with a subject, the method comprising the steps of:
    providing a valve system that includes a valve connector having a second portion of a first passageway and a second portion of a second passageway, the valve connector further including a suction port and an introduction port that are spaced apart and in substantially parallel alignment;
    attaching a nasogastric tube to the valve connector, the nasogastric tube including a first lumen and a second lumen, the first lumen defining a first portion of the first passageway, the second lumen defining a first portion of the second passageway, wherein the first passageway and the second passageway fluidly communicate adjacent a distal end of the nasogastric tube;
    inserting the distal end of the nasogastrie tube into the subject via a passage of the subject; and
    manipulating the suction port and the introduction port of the valve connector to establish fluid communication between the second portion of the first passageway and the suction port or the introduction port.

7. A method for administration of fluids with a subject as recited in claim 6, wherein the step of providing a valve system further includes a valve connector having a rotatable cap, the cap including the suction port and the introduction port such that the step of manipulating includes rotating the cap to establish fluid communication with the suction port for removing fluid from the subject.

8. A method for administration of fluids with a subject as recited in claim 6, wherein the step of providing a valve system further includes a valve connector having a rotatable cap, the cap including the suction port and the introduction port such that the step of manipulating includes rotating the cap to establish fluid communication with the introduction port for injecting fluid with the subject.

* * * * *